US00PP19773P2

(12) United States Plant Patent
Khemakongkanond

(10) Patent No.: US PP19,773 P2
(45) Date of Patent: Feb. 24, 2009

(54) ***DENDROBIUM* PLANT NAMED 'SPCDW0602'**

(50) Latin Name: *Dendrobium Sw.*
Varietal Denomination: SPCDW0602

(75) Inventor: Kanchana Khemakongkanond, Bangkok (TH)

(73) Assignee: Heike Suphachadiwong, Chonburi (TH)

( * ) Notice: Subject to any disclaimer, the term of this patent is extended or adjusted under 35 U.S.C. 154(b) by 0 days.

(21) Appl. No.: 11/827,202

(22) Filed: Jul. 11, 2007

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para

(57) ABSTRACT

A new cultivar of *Dendrobium* plant named 'SPCDW0602' that is characterized by a long main stem, large flowers that have white petals with pink highlights on the lip and long life as a cut flower.

1 Drawing Sheet

Botanical classification: *Dendrobium Sw.*
*Variety denomination: 'SPCDW*0602'.

BACKGROUND OF THE INVENTION

The present invention relates to a new and distinct cultivar of *Dendrobium* plant botanically known as *Dendrobium Sw.* and hereinafter referred to by the cultivar name 'SPCDW0602'.

The new cultivar was discovered as a naturally occurring branch mutation of *Dendrobium Sw.* 'Sonja' (not patented) in June of 2001. 'SPCDW0602' was discovered in an outdoor garden in a cultivated area of Bangkok, Thailand.

Asexual reproduction by tissue culture of the new cultivar 'SPCDW0602' was first performed in March of 2002 in Bangkok, Thailand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dendrobium* cultivar 'SPCDW0602'. These traits in combination distinguish 'SPCDW0602' as a new and distinct cultivar.

1. *Dendrobium* 'SPCDW0602' exhibits a long main stem.
2. *Dendrobium* 'SPCDW0602' exhibits large flowers that have white petals with pink highlights on the lip.
3. *Dendrobium* 'SPCDW0602' exhibits long life as a cut flower.

The new cultivar 'SPCDW0602' is distinguishable from the parent *Dendrobium* 'Sonja' by the following characteristics:

1. 'SPCDW0602' has white flowers. The flowers of 'Sonja' are purple.

The closest comparison cultivar is *Dendrobium* 'Emma White' (not patented). The new cultivar *Dendrobium* 'SPCDW0602' differs from 'Emma White' by the following characteristics:

1. 'SPCDW0602' has larger white flowers. 'Emma White' has flowers that have a green tint.

2. 'SPCDW0602' has a longer main stem than 'Emma White'.
3. 'SPCDW0602' has a lip tinged with pink. 'Emma White' does not.
4. 'SPCDW0602' has a larger overall height than 'Emma White'.

BRIEF DESCRIPTION OF THE DRAWING

The accompanying photograph illustrates the distinguishing traits of *Dendrobium* 'SPCDW0602'. The plant in the photograph shows an overall view of a 15 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dendrobium* cultivar named 'SPCDW0602'. Data was collected in Boskoop, The Netherlands from 24 month old plants grown outdoors in the shade in Bangkok, Thailand. The time of year was Spring. The average temperature was 30° Centigrade during the day and 26° Centigrade at night.

No photoperiodic treatments or growth retardants were used. Color determinations are in accordance with the Royal Horticultural Society Colour Chart 2001 edition, except where general color terms of ordinary dictionary significance are used. The growing requirements are similar to the species. 'SPCDW0602' has not been tested under all possible conditions and phenotypic differences may be observed with variations in environmental, climatic, and cultural conditions, however, without any variance in genotype.

Botanical classification: *Dendrobium Sw.* 'SPCDW0602'.
Parentage: 'SPCDW0602' is a naturally occurring branch mutation of *Dendrobium Sw.* 'Sonja'.
Vigor: Moderate.
Growth rate: Moderate.
Growth habit: Upright.
Plant shape: Monopodial with flowering stems growing from a basal rosette.

Height to top of flowers: Average 45.2 cm. in height.
Height to top of leaves: Average 29.4 cm. in height.
Width: Average 20.3 cm. in width.
Hardiness: USDA Zone 11.
Propagation: Tissue culture.
Time to initiate roots: Approximately 18 months to produce roots by tissue culture.
Time to produce a rooted cutting or liner: Approximately 9 months after tissue culture deflasking at 26–30° Centigrade.
Root system: Fleshy, rounded, slightly glossy, average diameter 1.5 mm.
Foliage:
*Texture.*—Smooth, glossy, slightly furrowed.
*Leaf arrangement.*—Alternate.
*Quantity of leaves per plant.*—8.
*Leaf shape.*—Narrow ovate.
*Leaf apex.*—Unequal acute.
*Leaf base.*—Sheathing.
*Leaf length.*—Average 11.9 cm. in length.
*Leaf width.*—Average 3.3 cm. in width.
*Pubescence.*—Absent.
*Leaf margin.*—Entire.
*Vein pattern.*—Camptodromous.
*Young leaf color* (*upper surface*).—Varies from 137A to 147A to 147B.
*Young leaf color* (*lower surface*).—Between 146A and 146B.
*Mature leaf color* (*upper surface*).—Varies from 137A to 147A to 147B.
*Mature leaf color* (*lower surface*).—146A to 146B.
*Vein color* (lower surface).—146A to 146B.
*Vein color* (*upper surface*).—137A to 147A to 147B.
*Durability of foliage to stress.*—High.
Flower:
*Flower arrangement.*—Terminal raceme.
*Inflorescence type.*—Raceme.
*Inflorescence dimensions.*—Average 10.5 cm. in diameter and 38 cm. in length.
*Flowering habit.*—Once a year.
*Flower form.*—Zygomorphic, typical *dendrobium* nobile shape.
*Quantity of flowers per inflorescence.*—Average 6.
*Quantity of flower stems per plant.*—Average 1.
*Quantity of flowers and buds per plant.*—Average 6.
*Flowering season.*—Late winter to spring.
*Time to flower or response time.*—10 months.
*Rate of flower opening.*—Lowest flowers of the raceme open first, all flowers will open in approximately 4 weeks.
*Fragrance.*—None.
*Self-cleaning or persistent.*—Self-cleaning.
*Flower bud length.*—2.9 cm. in length.
*Flower bud diameter.*—1.0 mm. in diameter.
*Flower bud shape.*—Ovate with a short mentum.
*Bud color.*—145B.
*Rate of bud opening.*—14 days.
*Flower aspect.*—Outward to moderately drooping.
*Flower shape.*—Zygomorphic.
*Vertical flower dimensions.*—5.9 cm.
*Horizontal flower dimensions.*—6.1 cm.
*Flower depth.*—4.2 cm.
*Flower longevity.*—Over 28 days.
*Petal appearance.*—Moderately glossy, slightly velvety.
*Petal texture.*—Glabrous.
*Petal arrangement.*—One petal one each side of the column.
*Number of petals.*—Two in number.
*Petals fused or unfused.*—Unfused.
*Petal shape.*—Obovate.
*Petal margin.*—Entire.
*Petal apex.*—Broad acute.
*Petal dimensions.*—4.1 cm. in length and 2.4 cm. in width.
*Petal color when opening* (upper side).—155A, apex 150D.
*Petal color when opening* (*under side*).—155A, upper half and apex 150D.
*Petal color when fully opened* (*upper side*).—N155A.
*Petal color when fully opened* (*under side*).—N155A.
*Petal color fading to.*—Not fading.
*Labellum appearance.*—Glabrous, dull.
*Labellum arrangement.*—Three-lobed.
*Labellum shape.*—Lobed, lateral lobes broad oblong, middle lobe obovate.
*Labellum tip.*—Lateral lobes obtuse, middle lobe broad acute.
*Labellum dimensions.*—Average 3.1 cm. in length and 1.8 cm. in width.
*Labellum color, young, upper side.*—1C to 1D, base 155A; callosities N155A.
*Labellum color, young, lower side.*—145C to 145D, base 155A.
*Labellum color, mature, upper side.*—N155A, callosities N155A, tinged 70D to 186D at the margins of the callosities.
*Labellum color, mature, lower side.*—N155A, callosities N155A.
Callosities:
*Callositie location.*—From the base to 75% of the central lobe of the labellum.
*Callositie dimensions.*—Average 2.5 cm in length and 5 mm in width (per callosity).
Sepals:
*Sepal appearance.*—Dull, smooth.
*Sepal arrangement.*—Two lateral sepals and one dorsal sepal.
*Number of sepals.*—Three in number.
*Sepal shape.*—Ovate.
*Sepal margin.*—Entire.
*Sepal tip.*—Acute.
*Sepal base.*—Cuneate.
*Lateral sepal length.*—Average 4.4 cm.
*Dorsal sepal length.*—Average 3.7 cm.
*Lateral sepal width.*—Average 1.8 cm.
*Dorsal sepal width.*—Average 1.6 cm.
*Lateral sepal color, immature, upper surface.*—145D.
*Lateral sepal color, immature, under surface.*—145C, fused mentum 145B.
*Dorsal sepal color, immature, under surface.*—145D.
*Dorsal sepal color, immature, upper surface.*—145D.
*Lateral sepal color, mature, upper surface.*—N155A.
*Lateral sepal color, mature, under surface.*—N155A, base 145D.
*Dorsal sepal color, mature, upper surface.*—N155A.
*Dorsal sepal color, mature, under surface.*—N155A.
Peduncle:
*Peduncle dimensions.*—Average 34.8 cm. in length and 4 mm. in diameter.
*Peduncle angle.*—20° from vertical.
*Peduncle color.*—144B.

*Peduncle strength.*—Strong.

Pedicels:

*Pedicel dimensions.*—Average 4.2 cm. in length and 3 mm. in diameter.

*Pedicel angle.*—45° from vertical.

*Pedicel color.*—157C to 157D, near peduncle 145B to 145D.

*Pedicel strength.*—Moderate to strong.

Reproduction organs:

*Column dimensions.*—Average 1.6 cm in length and 9 mm in width.

*Column color.*—N155A.

*Pollinia quantity.*—Moderate.

*Pollinia diameter.*—0.75 mm.

*Pollinia color.*—14B.

*Stigma shape.*—Rounded concave.

*Stigma color.*—147D.

*Stigma dimensions.*—4 mm in length and 4 mm in width.

*Ovary color.*—147D.

*Ovary dimensions.*—8 mm in length and 3 mm in diameter.

Seed: Seed production has not been observed.

Disease Resistance: Plants of the new *Dendrobium* are resistant to root diseases.

Pest resistance: Plants of the new *Dendrobium* have not been observed for pest resistance.

It is claimed:

1. A new and distinct variety of *Dendrobium* plant named 'SPCDW0602' as described and illustrated.

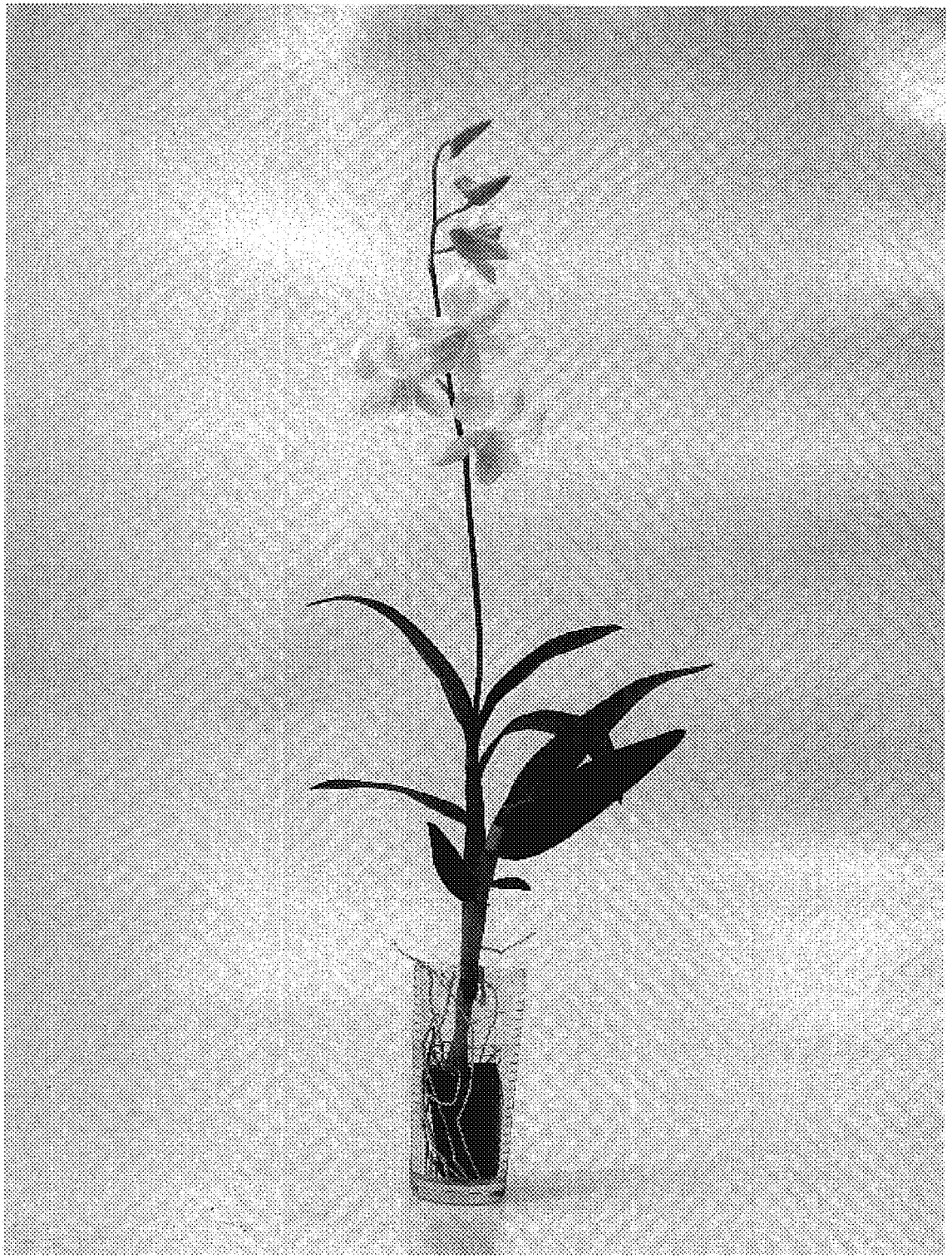

* * * * *